(12) United States Patent
Kohnz et al.

(10) Patent No.: US 8,809,600 B2
(45) Date of Patent: Aug. 19, 2014

(54) PROCESS FOR THE PRODUCTION OF LOWER ALCOHOLS BY OLEFIN HYDRATION

(76) Inventors: Harald Kohnz, Oberhausen (DE); Thomas Urban, Neukirchen-Vluyn (DE); Detlef Hoell, Moers (DE); Bernhard Pfeuffer, Varel (DE); Ulrich Hoffmann, Northeim (DE); Ulrich Kunz, Osterode (DE)

( * ) Notice: Subject to any disclaimer, the term of this patent is extended or adjusted under 35 U.S.C. 154(b) by 372 days.

(21) Appl. No.: 13/144,654

(22) PCT Filed: Jan. 14, 2010

(86) PCT No.: PCT/EP2010/000167
§ 371 (c)(1),
(2), (4) Date: Oct. 3, 2011

(87) PCT Pub. No.: WO2010/081700
PCT Pub. Date: Jul. 22, 2010

(65) Prior Publication Data
US 2012/0016164 A1    Jan. 19, 2012

(30) Foreign Application Priority Data

Jan. 15, 2009  (EP) ..................................... 09000517

(51) Int. Cl.
*C07C 29/04*    (2006.01)
*C12C 11/02*    (2006.01)

(52) U.S. Cl.
CPC ................ *C07C 29/04* (2013.01); *C12C 11/02* (2013.01)
USPC ....................................................... 568/895

(58) Field of Classification Search
None
See application file for complete search history.

(56) References Cited

U.S. PATENT DOCUMENTS

| | | | |
|---|---|---|---|
| 2,725,403 A * | 11/1955 | Hodgson | ...................... 568/901 |
| 2,933,460 A | 4/1960 | Richter et al. | |
| 3,055,729 A | 9/1962 | Richter et al. | |
| 3,965,039 A | 6/1976 | Chaplits et al. | |
| 3,996,298 A | 12/1976 | Izumi et al. | |
| 4,012,456 A | 3/1977 | Chaplits | |
| 4,139,565 A | 2/1979 | Unruh et al. | |
| 4,242,530 A | 12/1980 | Smith, Jr. | |
| 4,296,050 A | 10/1981 | Meier | |
| 4,340,769 A | 7/1982 | Brandes et al. | |
| 4,439,350 A | 3/1984 | Jones, Jr. | |
| 4,471,142 A | 9/1984 | Burton et al. | |
| 4,760,203 A | 7/1988 | Carls et al. | |
| 4,831,197 A | 5/1989 | Henn et al. | |
| 4,985,468 A | 1/1991 | Elmes et al. | |
| 5,552,056 A | 9/1996 | Ragosta | |
| 6,855,739 B2 | 2/2005 | Becker et al. | |
| 6,951,967 B2 * | 10/2005 | Gohrt et al. | ................... 568/895 |

FOREIGN PATENT DOCUMENTS

| | | |
|---|---|---|
| CH | 422306 | 4/1967 |
| CH | 437249 | 11/1967 |
| DE | 1569537 | 8/1969 |
| DE | 1904144 | 8/1970 |
| DE | 2147740 | 4/1973 |
| DE | 10012615 | 9/2001 |
| EP | 0130745 | 1/1985 |
| EP | 0428265 | 5/1991 |
| EP | 0664732 | 4/1994 |
| EP | 1199294 | 4/2002 |
| EP | 1574252 | 9/2005 |
| GB | 786238 | 11/1957 |
| GB | 2022129 | 12/1979 |
| WO | WO 2009/002603 | 12/2008 |

OTHER PUBLICATIONS

T.W. Leland et al., Phase Equilibriaum in 1-Butene Water System and Correlation of Hydrocarbon-Water Solubility Data, Industrial & Engineering Chemistry, 1955, p. 1265-1271.
Yoshioka, T., Studies of Polystyrne-based Ion Exchange Fiber I, Characteristics of Polystyrene-based Ion Exchange Fiber, The Chemical Society of Japan, 1983, p. 3726-3729.
Yoshioka, T., Studies of Polystyrene-based Ion-exchange Fiber III.-Chelating Exchanger and Properties of Heay Metal Ions, The Chemical Socieity of Japan, 1985, p. 2618-2625.
Pangarkar, et al., Structured Packings for Multiphase Catalytic Reactors, Ind. Eng. Chem. Res., 2008, p. 3720-3751.

* cited by examiner

*Primary Examiner* — Sudhakar Katakam
(74) *Attorney, Agent, or Firm* — Bushman & Associates, P.C.

(57) ABSTRACT

An improved process for the hydration of $C_2$-$C_5$ olefins to the corresponding alcohols via heterogeneous reactive extraction with ion exchange resin catalysts is provided. The improvements are based on the application of a structured catalytic packing, a simultaneous product extraction in multiple condensed phases for enhancement of the overall alcohol production rate and a simplified product purification procedure.

19 Claims, 6 Drawing Sheets

PROCESS FOR THE PRODUCTION OF LOWER ALCOHOLS BY OLEFIN HYDRATION

This application is a U.S. national phase of PCT/EP2010/000167 filed Jan. 14, 2009, and claims priority to EP 09000517.4 filed Jan. 15, 2009, the disclosures of which are incorporated herein by reference for all purposes.

The present invention relates to the production of lower alcohols by heterogeneously acid catalysed olefin hydration by the uses of structured catalysts preferably under simultaneous extraction. In particular concerned is an improved process for the production of isopropyl alcohol (IPA) by the catalytic reaction of propylene with water.

DESCRIPTION OF THE PRIOR ART

The hydration of olefins by the use of acids as catalysts is well known in the art. Early industrial processes were based on inorganic acids, e.g. sulphuric acid at high or low concentration (U.S. Pat. No. 4,471,142) employed in the liquid state. Corrosion problems, acid re-concentration, high energy demand and environmental concerns led to more modern techniques and the use of heterogeneous catalysts such as solid acid catalysts. As supported catalysts liquid acids based on phosphoric acid on an inorganic porous support were suggested in DE 1042561 A1, heteropolyacids in U.S. Pat. No. 3,996,298, zeolites in U.S. Pat. No. 1,395,65 and ion exchange resins in DE 2147740 A1.

Processes for the hydration of olefins employing ion exchange resins commonly operate at pressures in the range from 60 to 200 bar and temperatures between 120 and 180° C. When resins are used modern temperature resistant resins, such as Amberlyst 70 (Rohm and Haas) are preferred, such as those disclosed in EP 1,574,252 A1.

Ion exchange resin catalysts are generally randomly arranged on stages in continuously operated tubular reactors. Due to the very limited miscibility of propylene and water both components pass the catalyst bed in the form of separate phases (T. W. Leland et al., Ind. Eng. Chem. 1955(6), pp. 1265-1271). Such fixed bed reactors can operate in a co-current up flow such as taught in U.S. Pat. No. 4,760,203 or in a down flow as disclosed in DE 2,147,740. The resin is typically used in the form of beads with diameters in the range of 0.5 to 1.0 mm. The beads are randomly packed on such stages. An example of such a random packing is described in U.S. Pat. No. 4,831,197.

The hydration of olefins is a reversible exothermic reaction consuming water as the reactant. Many prior art processes, however, use additional water to remove heat. Typical molar feed ratios water/olefin therefore range from 10 to 20:1, an example of which is described for IPA in U.S. Pat. No. 4,340,769. The advantage of the process layout of U.S. Pat. No. 4,340,769 is a high olefin conversion rate but the product alcohol IPA exits the reactor as a diluted aqueous solution with concentrations ranging from 5 to 15 wt.-%. To recover pure IPA costly distillation processes are required.

OBJECT OF THE INVENTION

The hydration of olefins requires ion exchange resin catalysts with great mechanical strength in particular when high pressures and temperatures are involved. It has been found that many ion exchange resin catalysts deform due to the high pressure drop caused at high mass flow velocity. It is therefore one objective of the present invention to provide suitable catalyst arrangements for the hydration of olefins. A further object of the invention is to provide a new process for olefin hydration by arranging the acidic catalyst in structured packings.

SUMMARY OF THE INVENTION

The invention is defined in the independent claims. Preferred embodiments are the subject matter of the dependent claims or are described herein below.

The invention relates to a process for the continuous production of a lower aliphatic alcohol having from 2 to 5 carbon atoms, preferably having 3 to 5 carbon, most preferably having 3 or 4 carbon atoms, by the catalytic hydration of lower aliphatic olefins having 2 to 5 carbon atoms, preferably 3 to 5 carbon atoms, most preferably having 3 or 4 carbon atoms, in the presence of water and an immobilized strongly acidic structured catalyst preferably at a temperature of 80 to 220° C., in particular from 130 to 190° C., and a pressure of about 40 to 200 bar, in particular from 60 to 120 bar. As starting material linear olefins are preferred. Preferably each the olefin, the water and the alcohol are predominantly (by weight) in the liquid state during the reaction. Elevated pressures are necessary to keep all components in a condensed state, liquid and/or supercritical, wherein olefins such as propylene and water show a large miscibility gap. Due to the hydrophilic behaviour of the acidic resins the catalyst surface is always well wetted with water even at low water hold-up. This demands high pressures to dissolve the olefin in water and to transport the olefin to the active sites of the catalyst.

Caused by the arrangement of the catalyst, in particular the catalyst beads, an effective extraction occurs simultaneously with the formation of the alcohol. As a consequence recovery of the alcohol can be done by working up the organic phase instead of the aqueous phase as it is done in state of the art processes. Simultaneous extraction of the product alcohol exceeds chemical equilibrium limitations and improves the selectivity.

Structured catalysts are catalysts enabling high mass transfer and high interfacial areas for distributing and mixing the two nearly immiscible liquids in the aforementioned process of heterogeneous reactive extraction. Structured packings can be obtained by any kind of wrapping method for the catalyst particles and shaping the wrapped catalyst into fluid dynamically favourable arrangements.

In principal the structured catalysts used in the reactive extraction process of the present invention can be those known from reactive distillation processes. In the process of heterogeneous reactive extraction a structured catalyst ensures mass transfer between two liquid phases. In addition a structured catalyst can be installed in the reactor avoiding dead volumes and bypasses for the liquid flow, thereby leading to higher catalyst efficiency.

The present invention differs from conventional homogenous liquid-liquid extraction processes, wherein a liquid catalyst or a catalyst in the dissolved state, solved in at least one of the liquid phases is used in that the catalyst is an immobilized solid and a liquid-liquid extraction is employed in the presence of such catalyst. Such process may be called a heterogeneous reactive extraction process.

According to one embodiment of the process according to the present invention the acidic catalyst is immobilized in the form of a) A Structured Catalytic Packing.

According to a preferred form of above embodiment the catalyst, preferably in the form of particles/beads of approximately 0.5 to 5 mm diameter in size, is locked inside multiple, liquid permeable and shaped containments which insure good liquid distribution and mixing inside the reactor.

A suitable example of a structured catalytic packing is the commercially available catalyst Sulzer Chemtech Katapak, which consists of a wire mesh forming pockets filled with the catalyst. The catalyst is in particulate form. The liquid permeable wire mesh pockets are corrugated, by this shaping the mesh into a geometrical shape. This ensures good fluid distribution and mixing. The structured packing consists of layers of metal wire gauze in which the acid catalyst is embedded and thus immobilized in "pockets".

A further example is commercially available by the company CDTECH. Instead of wires glass fibre cloth is used to enclose the particulate catalyst, which is sewn into pockets. The pockets are filled with catalyst particles. In U.S. Pat. No. 4,242,530 such a catalyst arrangement is described in more detail. Today this technology is used by the CDTECH Company. Said catalyst arrangement consists of resin beads arranged in a plurality of pockets in a cloth belt. This belt is supported in the reacts for by open mesh knitted stainless steel wire by twisting belt and knitted mesh together. The knitted stainless steel mesh allows passage of two phase flow. By coiling the arrangements bales are formed which can be introduced inside the reactor an trays. Another example of a structured catalyst consists of vapour permeable plates which contain catalyst in a space between the plates.

Another approach is the shaping of the catalyst into a monolithic body to form b) A Monolithic Support Impregnated or Coated with the Acidic Catalyst.

This layout of a catalyst is known in the field of exhaust gas treatment catalysts for cars. Monoliths preferably have parallel channels whereby the channels are not necessarily interconnected. By impregnating such a monolith with acidic materials a well suited structuring for olefin hydration may be reached. Furthermore monolithic structured catalysts with the shape of honeycombs or other parallel channel structures known from exhaust gas catalysts in cars are suitable.

c) Acidic Fibres as Part of Woven or non Woven Fabrics

The structuring of the catalyst can be established by shaping the catalyst into acidic fibres as part of woven or non woven fabrics. This is explained in Yoshioka T., Bull. Chem. Soc. Japan 56, (1983), 3726-3729 and Yoshioka T., Bull. Chem. Soc. Japan 58, (1985) 26182625. The manufacture of ion exchange fibres is well known to those skilled in the art, see, for example, M. Lewin et al., "High Technology Fibers" Part B, Handbook of Fiber Science and Technology, Volume 111, Marcel Dekker, Inc., New York, 1989; U.S. Pat. No. 3,055,729 and U.S. Pat. No. 2,933,460, which are hereby incorporated by reference.

Materials such as the FIBAN-fibres (as mentioned in U.S. Pat. No. 5,552,056 A) can be suitable for heterogeneous reactive extraction for olefin hydration especially when the fibres are shaped into 3-dimensional structures. Such shaping into structured devices can be accomplished by weaving, knitting, crocheting, breading, stitching, knotting, twisting into ropes, as non woven fabrics, as felts or any other method that allows to design fibrous 3-dimensional structures with good heat and mass transfer properties and high interfacial area.

d) Catalytic Elements Aligned on Wires or Filaments

Catalytic elements aligned on wires or filaments are perforated catalyst particles on fibres, ropes, wires or any kind of filament, like a pearl necklace in jewellery and coiling this rope of pearls to larger arrangements by weaving, twisting, bending, braiding, knitting, knotting or crocheting. Another method can be the stitching of pearls on a cloth and shaping the pearl covered cloth into a three dimensional structure.

e) Catalytic Elements Formed by Foams or Sponges

Different to b) foams and sponges are porous solid materials with a random channel structure of the open pores. In addition for good liquid distribution and mixing gaps, slots in straight or corrugated kind may be cut into the sponge or foam.

With respect to the pore structure sponges and foams are like picture and mirror picture. For example foams are prepared by expansion of a gas in a polymer mixture. If such a porous polymer is filled with inorganic slurry and the polymer is burned off, the result is a sponge of the inorganic sintered material.

In recent years foams or sponges have been proven to be suitable for multiphase processes. Examples how to manufacture such materials are given in U.S. Pat. No. 4,985,468 and U.S. Pat. No. 6,855,739. It can be useful to introduce gaps, grooves or the like to guide fluid through the sponges/foams and or to distribute the liquids over the surface area of such materials to favour mass and heat transfer.

Above immobilized catalyst ensures excellent mass transfer between olefin and water phase, which form two nearly immiscible liquid phases under the reaction conditions. The Taylor flow regime known from gas-liquid processes may be used for the present liquid-liquid process as well.

Structured catalysts can be dispersed in the reactor, avoiding dead volume and bypassing of the two liquids to be contacted. Many different types of structured catalysts known from reactive distillation processes can be employed in the present process.

For the further definition and layout of structured catalytic packings it is referred to K. Pangarkar et al., Ind. Eng. Chem. Res. 2008, 47, pp. 3720-3751. The devices of which are disclosed therein, are herewith made of reference for the present application.

Some particular preferred catalyst designs that can suitably be employed in the process according to the present invention are described in WO 90/02603. The structured catalytic packings according to WO 90/02603 comprises a plurality of layers with flow channels between said layers for a flow of reactants, therein said layers having walls defining an interspace there between; and a catalyst material in each interspace of said layers, wherein the walls are made of a material permeable to the reactants but impermeable to the catalyst material to permit a catalyzed reaction of the reactants within said interspaces. The device further comprises a plurality of guide elements spacing said layers from each other and defining said flow channels. The guide elements are preferably made of corrugated plates and/or rod element. The guide elements may be angularly disposed with respect to a longitudinal axis of a respective layer. The layers may be made of wire cloth and knitted wire fabric and of materials such as metal, glass and plastic.

The layout of the reactor may comprise a housing having an admission space for reactants and a delivery space for drawing off reactants and products; a plurality of tubes connecting said spaces with each other; a plurality of devices disposed in each tube for a catalyzed reaction therein, each said device including a plurality of layers disposed in relation with flow channels between said layers for reactants, each said layer defining an interspace therein; and a catalyst material in each interspace of said layers, each said layer being made of a material permeable to the reactants and impermeable to said catalyst material to permit a catalyzed reaction in a respective interspace; a tube connection in said housing for supplying a heat conveying medium to a heat exchange space about said tubes; and a tube connection in said housing for moving the medium from said heat exchange space.

Other suitable layouts of structured catalysts are described in EP 0,428,265 A1, U.S. Pat. No. 4,242,530, U.S. Pat. No. 4,439,350, DE 1904144 A1, U.S. Pat. No. 4,296,050 and EP 0130745 A2, EP 0664732, DE 10012615. U.S. Pat. No. 3,965,039 and U.S. Pat. No. 4,012,456, DE 1569537, CH 422306 and CH 437249.

Structured packings are called the three-dimensional structures forming the catalyst containing pockets. Particularly preferred for use in the claimed process are stainless steel wire mesh packings, such as Sulzer Chemtech Katapak, and bale packings, as offered by CDTECH.

The catalysts is an acidic solid material e.g. ion exchange resins, composites made of ion exchange resins with porous carrier materials, heteropolyacids, impregnated supports with strong mineral acids, zeolites or any acidic material which is stable under the process conditions of the present process. All catalysts are preferably in the form of particles when used in the structured catalytic packings.

One preferred aspect of the invention is the application of a structured packing filled with ion exchange resin catalysts. Thus, the applicability of commercially available ion exchange resin catalyst is enlarged even to mechanically less stress resistant polymers (brittle or soft, gel type or macro reticular). The structured packing aerates the wetted catalyst avoiding large lumps of catalyst to be formed which are impenetrable by the olefin flow. This property of the structured packing in combination with the excellent wetting by water leads to high interfacial surface areas and thereby enhances mass transfer. In addition the olefin is well distributed all over the structured catalytic packing efficiently penetrating the wet catalyst.

When using a structured metal packing the radial heat transfer is improved. The well defined distribution of reactants and the catalyst guaranties a uniform heat generation avoiding clusters of overheated catalyst. This prevents also the oligomerisation of propylene. Thus, the catalyst is less stressed by thermal and chemical attack extending its lifetime.

Furthermore, the structured packing decreases the heat generation rate per reactor volume by spacing the catalyst within the reactor. The heat of reaction for IPA formation by propylene hydration with 51.4 kJ/mole is moderate and the generated amount of heat can be removed by well known procedures, e.g. multibed adiabatic reactors with intersectional heat exchangers or cooled multitube reactors.

Due to the application of structured packings as is proposed herein the water hold-up and consequently the water feed can be reduced significantly. Coming to a higher propylene feed an organic phase is established which efficiently extracts the IPA from the catalyst. The simultaneous extraction of the IPA avoids the unwanted formation of ether and enlarges the distance to the chemical equilibrium. Product recovery from such an organic phase is easier achieved than from the commonly produced aqueous phase. The aqueous phase withdrawn from the reactor outlet is separated from the organic phase by decantation and can be recycled to the reactor inlet. The recyclate has to be treated with anion exchange resins to trap acidic ions which can be dissolved from the acidic catalyst in the reactor.

Extraction occurs parallel and simultaneously with the formation of the alcohols. The obtained alcohol is preferably extracted from the water phase existing on the phase boundary made up between the surface of the water comprising film and the organic phase flooding the empty space within the structured packings. The outlet streams are preferably worked up by heteroazeotropic distillation.

The reaction conditions are preferably such that multiple condensed phases are formed in the reactor. This is achieved by applying a pressure to the reactor which ensures to keep the water in the liquid state and the olefin in the liquid or supercritical state, respectively.

Under such conditions it is found that water and olefin are nearly immiscible in the condensed state for process conditions ranging from 80 to 220° C. and from 40 to 200 bar, in particular ranging from 130 to 190° C. and from 60 to 120 bar.

In summary the reactive extraction in combination with the application of a structured catalytic packing and the improved product recovery present enormous process intensification. According to one embodiment of the invention the enhancement of the overall chemical reaction rate is achieved by simultaneous extraction in multiple condensed phases.

The best results were found when using propylene as the stationary phase and water as the mobile phase flowing downwards through the structured catalytic packing and separating IPA from the organic phase. A space-time yield (STY) of max. 7.96 $mole_{IPA}/ltr_{cat}/hr$ was observed compared to 4.79 $mole_{IPA}/ltr_{cat}/hr$ in an experimental setup without structured packing. A further advantage of this Operation mode in particular for IPA production is a low pressure drop even at high flow rates.

Below given examples show how structured catalytic packings can be used advantageously. A high hold-up of the organic phase and a low load of the trickling aqueous phase inside the structured packing are the key factors for improved alcohol production. In addition the pressure drop is significantly reduced so that an additional surfactant as recommended in U.S. Pat. No. 4,831,197 is no longer necessary.

Though, the experiments presented here were performed in a counter-current flow mode it is obvious that co-current flow mode from the reactor design and Layout is easier to realise.

DETAILED DESCRIPTION OF THE INVENTION

The invention is further detailed with reference to the figures without that the figures are construed to limit the scope of the invention to the embodiments depicted.

Figure 1:
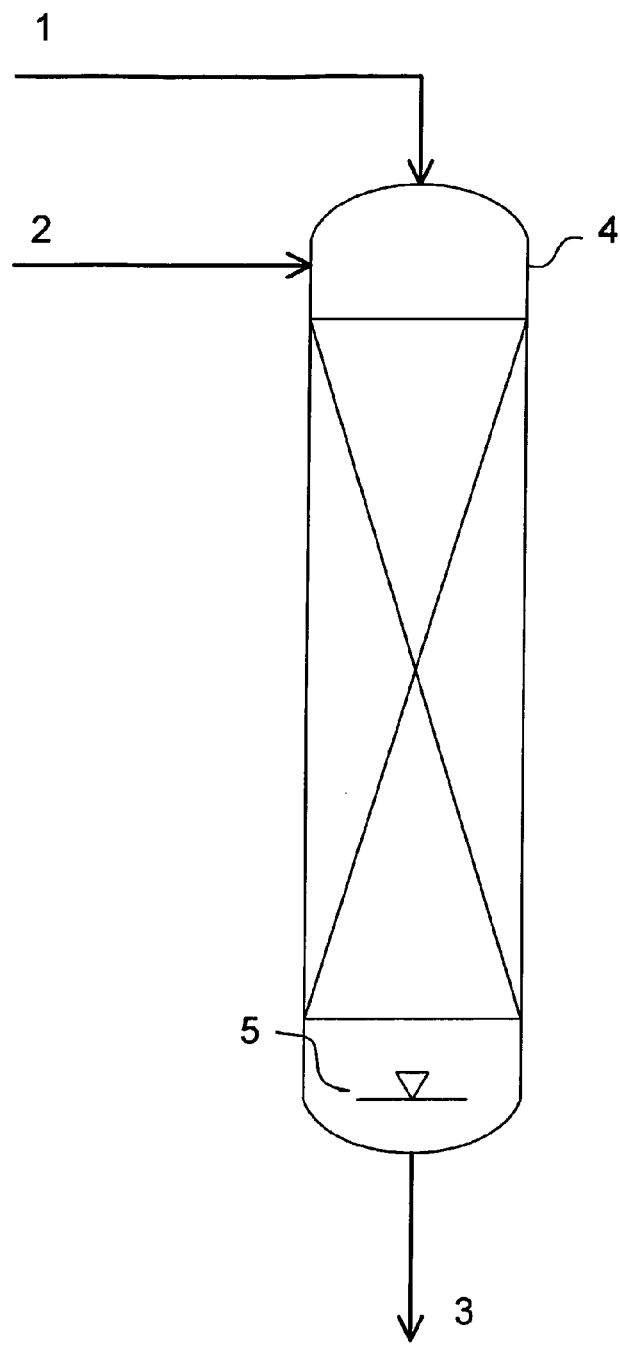
FIG. 1: a set up of an apparatus for evaluating the catalyst.

Surprisingly high space time yields (STY) were observed in the test apparatus as depicted in FIG. 1 even for traditional resin catalysts for the below given superficial mass flow velocities (G) described in Table 1. The operating pressure was set to 90 bar.

TABLE 1

Comparison of random and structured packing for IPA production

|  | catalyst A operated at temperature limit of 160° C. | | catalyst B operated at 170° C. temperature limit 190° C. | |
| --- | --- | --- | --- | --- |
|  | random packing | structured packing | random packing | structured packing |
| STY [$mole_{IPA}/ltr_{cat}/hr$] | 3.34 | 5.37 | 4.79 | 7.96 |
| G [$kg/m^2/s$] | 0.78 | 0.29 | 0.78 | 0.29 |

Figure 2:
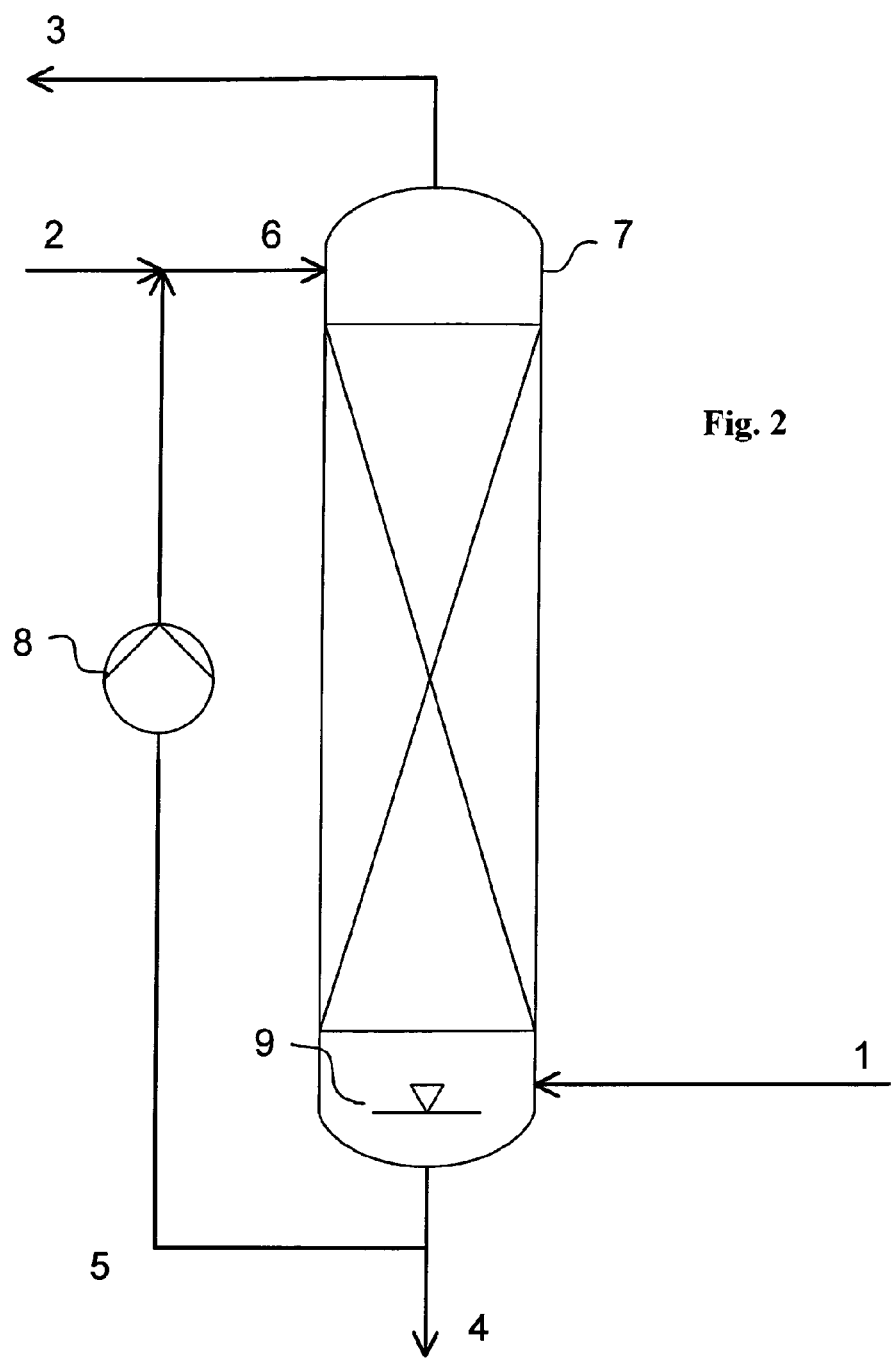
FIG. 2: a laboratory column reactor with structured catalytic packing for olefin hydration with separation layer at the bottom.
Figure 3:
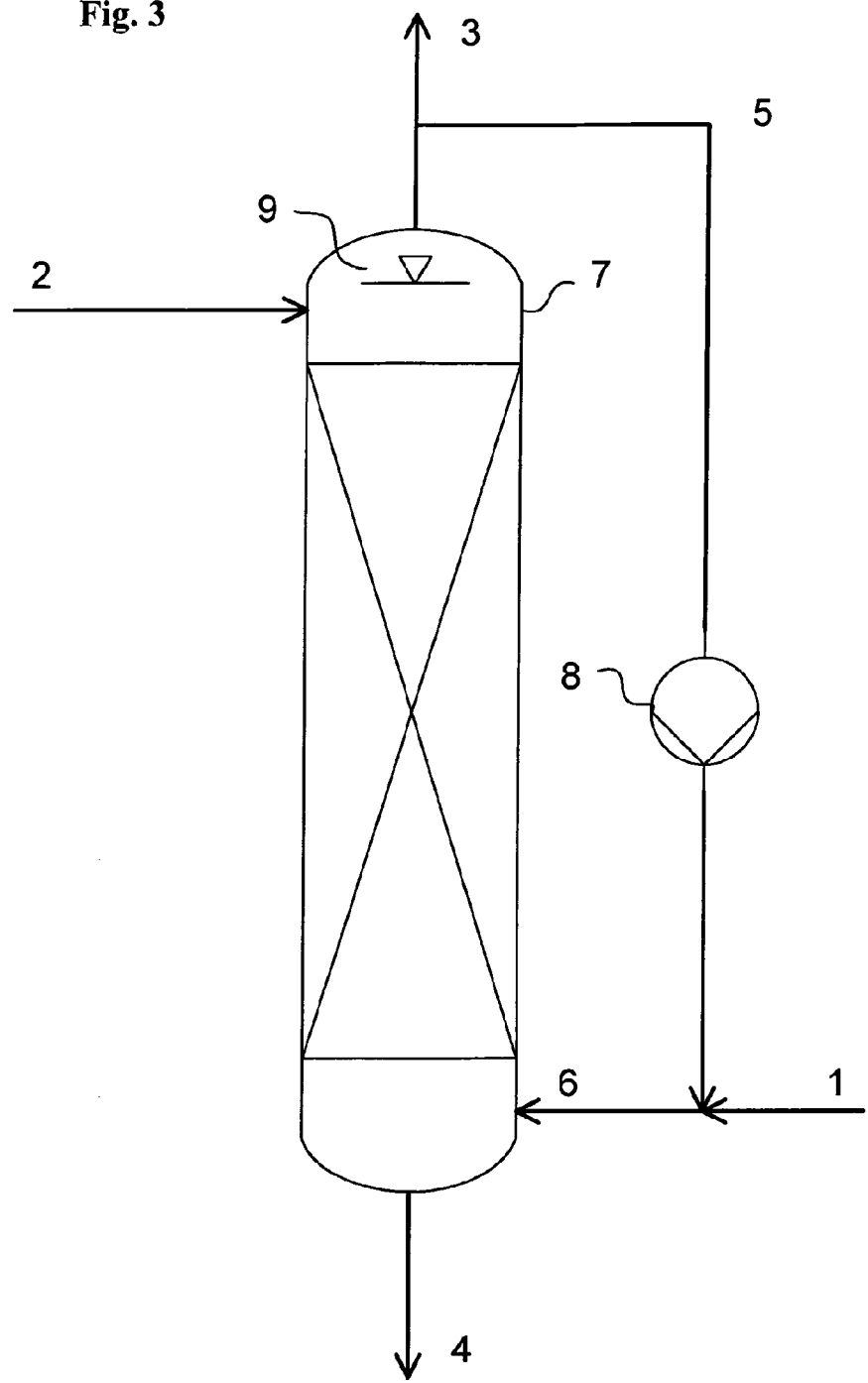
FIG. 3: a laboratory column reactor with structured catalytic packing for olefin hydration with separation layer at the top.

In the following examples further results are given showing the improvements in alcohol production by the application of a structured packing in combination with extraction. The examples concern the hydration of n-butylenes and propylene to 2-butyl alcohol (SBA) and isopropyl alcohol (IPA), respectively. All experiments were performed in a laboratoiy column reactor equipped with structured catalytic packing as depicted in FIGS. 2 and 3.

EXAMPLE 1

Butylenes were used as the olefins for the comparison of different flow and hold-up situations. In the FIGS. 2 and 3 the reactor 7 is fed by the olefin inlet stream 1 and the water inlet stream 2. The reactor is equipped with a structured catalytic packing (Sulzer Chemtech Katapak) and an adequate temperature control. Stream 3 is the organic phase outlet and stream 4 is the aqueous phase outlet. The minor part of stream 3 served as purge stream. The recycle stream 5 is moved by pump 8 and is combined with a feed stream to the reactor inlet stream 6. Number 9 marks the position of the phase boundary layer between organic and aqueous phase.

Four different Operation modes were investigated:
a) Butylenes were the stationary phase and water was the mobile phase. Separation layer 9 was below the catalytic packing, see FIG. 2. Recovery of SBA was done from the aqueous phase, stream 4. There was no recycle, stream 5 was zero. By feeding 1980 gr/hr of water (stream 2) a reaction product of 1999 gr/hr (stream 4) was removed. This product stream contained 1.16 wt.-% of SBA, the achieved STY was 0.78 $moles_{SBA}/ltr_{cat}/hr$. Reacted butylenes were added via a pressure control system over stream 1 with a calculated amount of app. 19 gr/hr.
b) Butylenes were the stationary phase and water was the mobile phase. Separation layer 9 was below the catalytic packing, see FIG. 2. Recovery of SBA was done from the organic phase, stream 3. The major part of the aqueous phase outlet stream 4 was recycled by stream 5. By feeding 990 gr/hr of butylenes (stream 1) a reaction product of 1016 gr/hr (stream 3) was removed. This product stream contained 5.28 wt.-% of SBA, the achieved STY was 1.81 $mole_{SBA}/ltr_{cat}/hr$. Reacted water was added via a level control system for phase boundary layer over stream 2 with a calculated amount of app. 26 gr/hr.
c) Water was the stationary phase and the butylenes were the mobile phase. Separation layer 9 was above the catalytic packing, see FIG. 3. Recovery of SBA was done from the aqueous phase, stream 4. The major part of the organic phase outlet stream 3 was recycled by stream 5. By feeding 1010 gr/hr of water (stream 2) a reaction product of 1017 gr/hr (stream 4) was removed. This product stream contained 0.93 wt.-% of SBA, the achieved STY was 0.32 $moles_{SBA}/ltr_{cat}/hr$. Reacted butylenes were added via a pressure control system over stream 1 with a calculated amount of app. 7 gr/hr.
d) Water was the stationary phase and the butylenes were the mobile phase. Separation layer 9 was above the catalytic packing, see FIG. 3. Recovery of SBA was done from the organic phase, stream 3. There was no recycle, stream 5 was zero. By feeding 500 gr/hr of butylenes (stream 1) a reaction product of 515 gr/hr (stream 3) was removed. This product stream contained 3.13 wt.-% of SBA, the achieved STY was 0.54 $mole_{SBA}/ltr_{cat}/hr$. Reacted water was added via a level control system for phase boundary layer over stream 2 with a calculated amount of app. 15 gr/hr.

The results of these Operation modes are summarized in Tab. 2.

TABLE 2

Test results for SBA production

| operation |  | mode a | mode b | mode c | mode d |
| --- | --- | --- | --- | --- | --- |
| catalyst | type | B | B | B | B |
| cat. volume | ltr. | 0.40 | 0.40 | 0.40 | 0.40 |
| pressure | bar | app. 90 | app. 90 | app. 90 | app. 90 |
| temperature | ° C. | 170 | 170 | 170 | 170 |
| STY | $mole_{SBA}/ltr_{cat}/hr$ | 0.78 | 1.81 | 0.32 | 0.54 |
| stream 1 | gr/hr | app. 19 [x)] | 990 | app. 7 [x)] | 500 |
| stream 2 | gr/hr | 1980 | app. 26 [y)] | 1010 | app. 15 [y)] |
| stream 3 | gr/hr | 0 | 1016 | 0 | 515 |
| stream 4 | gr/hr | 1999 | 0 | 1017 | 0 |
| stream 5 | gr/hr | 0 | 2000 | 1000 | 0 |

[x)] fed via pressure control system
[y)] fed via level control system for phase boundary layer The best results were achieved when using butylenes as the stationary phase and water as the mobile phase flowing downward through the structured catalytic packing and separating SBA from the organic phase. A space-time yield (STY) of max. 1.8 $mole_{SBA}/ltr_{cat}/hr$ was achieved compared to 1.4 $mole_{SBA}/ltr_{cat}/hr$ in an experimental setup without a structured packing. Further advantages of this Operation mode for SBA production are low ether formation and avoiding pressure drop problems at high flow rates.

EXAMPLE 2

Propylene was used as the olefin for the comparison of different flow and hold-up situations. In the FIGS. 2 and 3 the reactor 7 is fed by the olefin inlet stream 1 and the water inlet stream 2. The reactor is equipped with a structured catalytic packing and an adequate temperature control. Stream 3 is the organic phase outlet and stream 4 is the aqueous phase outlet. The minor part of stream 3 served as purge stream. The recycle stream 5 is moved by pump 8 and is combined with a feed stream to the reactor inlet stream 6. Number 9 marks the position of the phase boundary layer between organic and aqueous phase.

Four different operation modes were investigated:
a) Propylene was the stationary phase and water was the mobile phase. Separation layer 9 was below the catalytic packing, see FIG. 2. Recovery of IPA was done from the aqueous phase, stream 4. There was no recycle, stream 5 was zero. By feeding 1981 gr/hr of water (stream 2) a reaction product of 2110 gr/hr (stream 4) was removed. This product stream contained 9.36 wt.-% of IPA, the achieved STY was 5.48 $mol_{IPA}/ltr_{cat}/hr$. Reacted propylene was added via a pressure control system over stream 1 with a calculated amount of app. 129 gr/hr.

b) Propylene was the stationary phase and water was the mobile phase. Separation layer 9 was below the catalytic packing, see FIG. 2. Recovery of IPA was done from the organic phase, stream 3. The major part of the aqueous phase outlet stream 4 was recycled by stream 5. By feeding 2010 gr/hr of propylene (stream 1) a reaction product of 2120 gr/hr (stream 3) was removed. This product stream contained 13.55 wt.-% of IPA, the achieved STY was 7.96 $mole_{IPA}/ltr_{cat}$/hr. Reacted water was added via a level control system for phase boundary layer over stream 2 with a calculated amount of app. 110 gr/hr.

c) Water was the stationary phase and propylene was the mobile phase. Separation layer 9 was above the catalytic packing, see FIG. 3. Recovery of IPA was done from the aqueous phase, stream 4. The major part of the organic phase outlet stream 3 was recycled by stream 5. By feeding 978 gr/hr of water (stream 2) a reaction product of 1016 gr/hr (stream 4) was removed. This product stream contained 5.17 wt.-% of IPA, the achieved STY was 1.62 $mole_{IPA}/ltr_{cat}$/hr. Reacted propylene was added via a pressure control system over stream 1 with a calculated amount of app. 38 gr/hr.

d) Water was the stationary phase and propylene was the mobile phase. Separation layer 9 was above the catalytic packing, see FIG. 3. Recovery of IPA was done from the organic phase, stream 3. There was no recycle, stream 5 was zero. By feeding 980 gr/hr of propylene (stream 1) a reaction product of 1022 gr/hr (stream 3) was removed. This product stream contained 9.18 wt.-% of IPA, to the achieved STY was 2.89 $mole_{IPA}/ltr_{cat}$/hr. Reacted water was added via a level control system for phase boundary layer over stream 2 with a calculated amount of app. 42 gr/hr.

The results of these operation modes are summarized in Tab. 3.

TABLE 3

Test results for IPA production

| operation | | mode a | mode b | mode c | mode d |
|---|---|---|---|---|---|
| catalyst | type | B | B | B | B |
| cat. volume | ltr. | 0.60 | 0.60 | 0.54 | 0.54 |
| pressure | bar | app. 90 | app. 90 | app. 90 | app. 90 |
| temperature | ° C. | 170 | 170 | 170 | 170 |
| STY | $mole_{IPA}/ltr_{cat}$/hr | 5.48 | 7.96 | 1.62 | 2.89 |
| stream 1 | gr/hr | app. 129 [x)] | 2010 | app. 38 [x)] | 980 |
| stream 2 | gr/hr | 1981 | app. 110 [y)] | 978 | app. 42 [y)] |
| stream 3 | gr/hr | 0 | 2120 | 0 | 1022 |
| stream 4 | gr/hr | 2110 | 0 | 1016 | 0 |
| stream 5 | gr/hr | 0 | 2000 | 2000 | 2000 |

[x)] fed via pressure control system
[y)] fed via level control system for phase boundary layer The formation of $C_2$-$C_5$ alcohols by olefin hydration is exothermic. For instance, the heat of reaction for IPA production of 51.4 kJ/mole is moderate and even lower for the higher alcohols.

Figure 4:
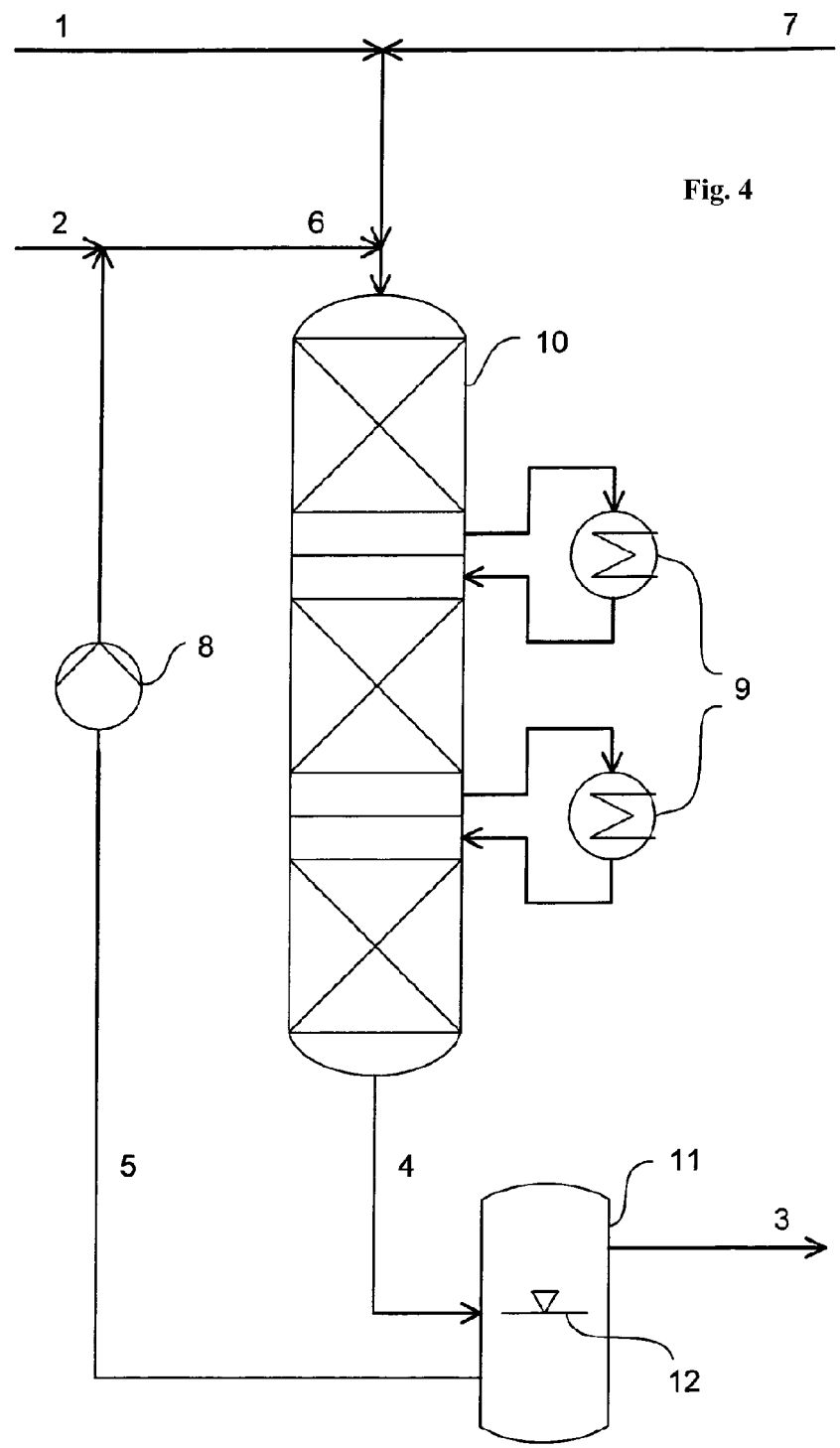
FIG. 4: a scheme of the multibed adiabatic reactor with intersectional heat exchange.
Figure 5:
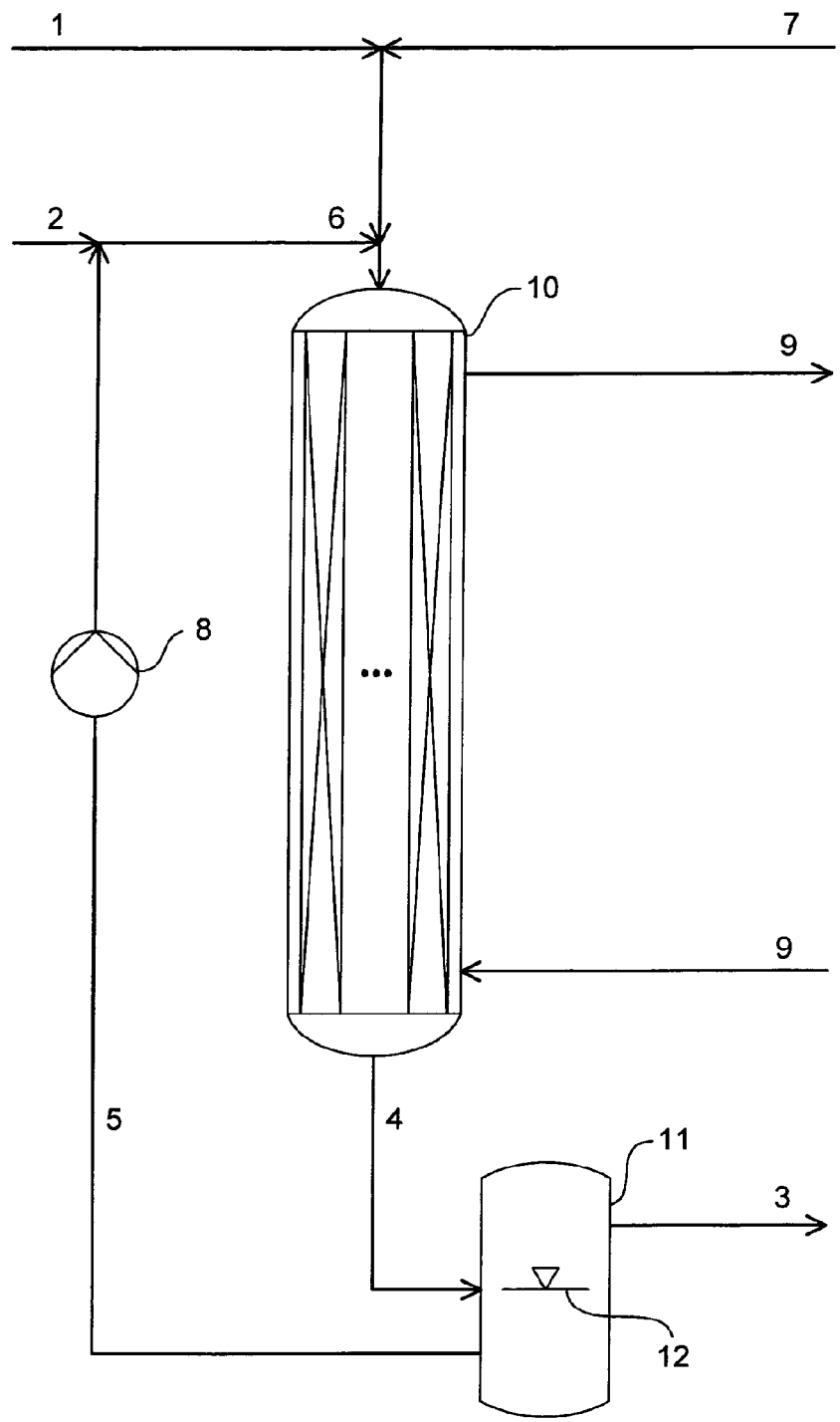
FIG. 5: a multitube reactor with heat exchange.

The generated amount of heat can be removed, e.g. by multibed adiabatic reactors with intersectional heat exchangers or cooled multitube reactors. Simplified sketches showing the flow directions of the components with two heat removal concepts are depicted in FIGS. 4 & 5. Co-current flow and/or counter-current flow are also possible. Structured packings with high thermal conductivities are beneficial.

State of the art in IPA production is the refinement of the aqueous phase. According to one embodiment of the present invention the organic phase is refined. This concept reduces the energy consumption necessary for evaporating huge amounts of water which has a high heat of vaporisation. The reactor is operated in such a way that in the organic phase the molar ratio of water to IPA is always less than one. This can be reached by appropriate short residence times of the organic phase since the mass transfer rate into the organic phase for alcohol is is higher than for water and is additionally limited by the physical equilibrium between the coexisting condensed phases. As a consequence, the separation units can be simplified. The presently used conventional distillation column for alcohol enrichment from the dilute aqueous phase can be avoided and can be replaced by a simple stripper to separate the unconverted propylene.

Figure 6:
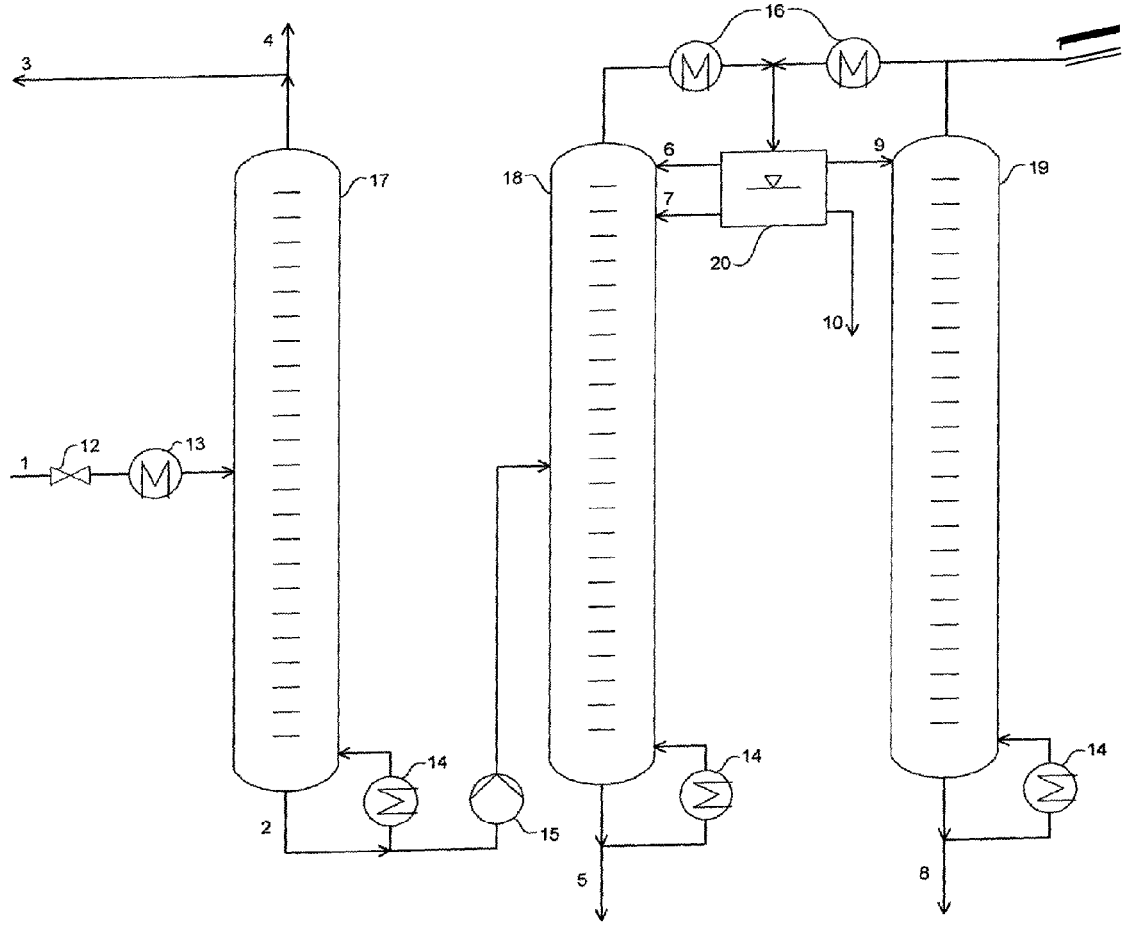
FIG. 6: a scheme of the separation procedure according to the present invention.

It is state of the art to use such a stripper for the easy separation of mixtures containing components having wide range of boiling points ($T_{b,propene}$ app. 225 K; $T_{b,isopropanol}$ app. 355 K; $T_{b,water}$ app. 373 K; all at 1 atm). The IPA containing bottom stream from the stripper is fed to the currently used IPA purification units. A sketch of the simplified separation procedure is depicted in FIG. 6. The stripper can be operated without auxiliary stripping gas. This is due to the large amount (greater 60 mole-%) of propylene in the mixture supposed for separation. In one preferred embodiment of the present invention the pressure level in the stripper should be close to atmospheric conditions. The top stream 3 is recycled to the reactor whereas purge stream 4 avoids accumulation of inerts in the recycle stream.

Table of Reference Numbers for FIGS. 1 to 6

FIG. 1:

| | |
|---|---|
| 1 | water feed |
| 2 | olefin feed |
| 3 | aqueous phase exit |
| 4 | laboratory column with structured catalytic packing |
| 5 | phase boundary layer |

FIG. 2:

| | |
|---|---|
| 1 | olefin feed |
| 2 | water feed |
| 3 | organic phase exit |
| 4 | aqueous phase exit |
| 5 | aqueous recycle |
| 6 | combined water feed and aqueous phase recycle |
| 7 | laboratory column with structured catalytic packing |
| 8 | recycle pump |
| 9 | phase boundary layer |

FIG. 3:

| | |
|---|---|
| 1 | olefin feed |
| 2 | water feed |
| 3 | organic phase exit |
| 4 | aqueous phase exit |
| 5 | organic recycle |
| 6 | combined olefin feed and organic phase recycle |
| 7 | laboratory column with structured catalytic packing |
| 8 | recycle pump |
| 9 | phase boundary layer |

FIG. 4:

| | |
|---|---|
| 1 | olefin feed |
| 2 | water feed |
| 3 | organic phase exit |
| 4 | reactor outlet |
| 5 | aqueous phase recycle |
| 6 | combined water feed and aqueous phase recycle |
| 7 | olefin recycle from product recovery |
| 8 | recycle pump |
| 9 | heat exchangers |
| 10 | multibed adiabatic reactor with structured catalytic packing |
| 11 | decanter |
| 12 | phase boundary layer |

Table of Reference Numbers for FIGS. 1 to 6

FIG. 5:

| | |
|---|---|
| 1 | olefin feed |
| 2 | water feed |
| 3 | organic phase exit |
| 4 | reactor outlet |
| 5 | aqueous phase recycle |
| 6 | combined water feed and aqueous phase recycle |
| 7 | olefin recycle from product recovery |
| 8 | recycle pump |
| 9 | cooling medium intake/outlet |
| 10 | multitube reactor with structured catalytic packing |
| 11 | decanter |
| 12 | phase boundary layer |

FIG. 6:

| | |
|---|---|
| 1 | organic phase feed |
| 2 | bottom product stripper |
| 3 | olefin recycle to reactor |
| 4 | olefin purge |
| 5 | purified alcohol azeotropic distillation |
| 6 | organic phase recycle azeotropic distillation |
| 7 | aqueous phase recycle azeotropic distillation |
| 8 | purified alcohol standard distillation |
| 9 | organic phase recycle standard distillation |
| 10 | aqueous phase recycle to reactor |
| 11 | diisopropyl ether/hexane outlet |
| 12 | pressure reducing valve |
| 13 | heat exchanger |
| 14 | reboiler |
| 15 | pump |
| 16 | total condenser |
| 17 | stripping column |
| 18 | azeotropic distillation column |
| 19 | standard distillation column |
| 20 | decanter |

The invention claimed is:

1. Process for the hydration of olefins to alcohols at pressures of 40 to 200 bar and a temperature of 80 to 200° C. by heterogeneous reactive extracting bringing into contact in a reactor one or more olefins having 3 or 4 carbon atoms, water and an acidic catalyst comprising an ion exchange resin, wherein the acidic catalyst is immobilized and selected from at least one of the following structured catalysts:
   a) a structured catalytic packing wherein the structured catalyst comprises multiple flow through channels wherein first multiple channels are orientated with an angle of +20 to +60° and second multiple channels with an angle of −20 to −60° towards the flow direction and the first and the second channels provide for multiple intersections to allow mass transfer in multiple directions;
   b) a monolithic support having the shape of honeycombs or other parallel channel structures, impregnated or coated with the acidic catalyst;
   c) acidic fibres as part of woven or non woven fabrics; and
   d) catalytic elements aligned an wires or filaments.

2. The process according to claim 1, wherein in the reactor the water and the olefin are present in multiple condensed phases.

3. The process according to claim 1, wherein the olefin is propylene and the alcohol is isopropanol.

4. The process according to claim 1, wherein the structured catalytic packing comprises multiple flow through channels and multiple cages permeable to the olefin and water but enclosing the acidic catalyst in the form of beads.

5. The process according to claim 1, wherein a volumetric olefin/water hold-up ratio of from 10:1 to 20:1 is used and the hold-up ratio is maintained by a catalyst load of from 10 to 60 vol.-%.

6. The process according to claim 1, wherein the flooding conditions affecting the hold-up ratio in the structured packing are controlled by the feed streams of olefin and water.

7. The process according to claim 1, wherein the product alcohol is recovered from the aqueous phase by extraction with the olefinic phase.

8. The process according to claim 1, wherein the space-time yield (STY) is above of 5 $mole_{IPA}/ltr_{cat}/hr$ when IPA is the product or wherein the space-time yield (STY) is above of 1.8 $mole_{IPA}/ltr_{cat}/hr$ when SBA is the product.

9. The process according to claim 1, wherein the structured acidic catalyst a) to d) according to claim 1 is made of a corrosion resistant metal and/or glass.

10. The process according to claim 1, wherein said catalytic packing is used in combination with separation sections in the reactor.

11. The process according to claim 1, wherein the molar feed ratio of the reactants is adjusted by variation of the feed streams into the reactor to maintain a volumetric olefin hold-up inside the hydration reactor ranging from 36 to 86 vol.-%.

12. The process according to claim 1, wherein the reactor outlet mixture is separated by decantation into a condensed organic phase and a liquid aqueous phase wherein the aqueous phase can be recycled to the reactor inlet.

13. The process according to claim 1, wherein unconverted olefins are recovered from the condensed organic phase by a separation process prior to azeotropic distillation used for alcohol purification.

14. The process according to claim 13, wherein said separation process is a stripping process.

15. The process according to claim 14 wherein said separation process separates gaseous propylene from the isopropyl alcohol containing inlet stream of the azeotropic distillation.

16. The process according to claim 13, wherein the unconverted olefin is propylene and wherein the azeotropic distillation is used for isopropyl alcohol purification.

17. The process according to claim 16 wherein said separation process is a stripping process.

18. The process according to claim 17 wherein said separation process separates gaseous propylene from the isopropyl alcohol containing inlet stream of the azeotropic distillation.

19. The process according to claim 1, wherein the olefin is the stationary phase and water is the mobile phase preferably flowing downwards through the structured catalyst.

* * * * *